United States Patent [19]

Kerwin

[11] Patent Number: 4,963,135
[45] Date of Patent: Oct. 16, 1990

[54] FLOATATION CHAMBER FOR USE IN A CHEST DRAINAGE DEVICE

[75] Inventor: Michael J. Kerwin, St. Louis, Mo.

[73] Assignee: Sherwood Medical Company, St. Louis, Mo.

[21] Appl. No.: 363,749

[22] Filed: Jun. 9, 1989

[51] Int. Cl.$^5$ ............................................. A61M 1/00
[52] U.S. Cl. ................................. 604/320; 604/321; 137/205
[58] Field of Search .................... 604/317, 319–321; 137/205

[56] References Cited

U.S. PATENT DOCUMENTS

| | | | |
|---|---|---|---|
| 3,683,913 | 8/1972 | Kurtz et al. | 128/276 |
| 3,809,085 | 5/1974 | Bidwell et al. | 128/275 |
| 3,960,165 | 6/1976 | Holbrook et al. | 137/202 |
| 4,195,633 | 4/1980 | Nehring et al. | 128/276 |
| 4,289,158 | 9/1981 | Nehring | 137/205 |
| 4,439,189 | 5/1984 | Sargeant et al. | 604/317 |
| 4,439,190 | 3/1984 | Protzmann et al. | 604/319 |
| 4,455,141 | 6/1984 | Todd | 604/319 |
| 4,519,796 | 5/1985 | Russo | 604/319 |
| 4,601,715 | 7/1986 | Olson | 604/321 |
| 4,650,477 | 3/1987 | Johnson | 604/321 |
| 4,767,417 | 8/1988 | Boehringer et al. | 604/31 |
| 4,781,707 | 11/1988 | Boehringer et al. | 604/317 |
| 4,784,642 | 11/1988 | Everett, Jr. | 604/320 |

Primary Examiner—Randall L. Green
Assistant Examiner—K. Reichle
Attorney, Agent, or Firm—Andrew J. Beck; Montgomery W. Smith; Richard D. Allison

[57] ABSTRACT

A chest drainage device having a collection chamber, a water seal chamber and a suction control chamber wherein the suction control chamber includes first and second columns and wherein the top end of the first column is open to the atmosphere and the top end of the second column is in flow communication with a vacuum source. The bottom end of the first and second columns are preferably in flow communication with a float chamber to increase the effective dynamic water height of the liquid in the suction chamber and to decrease the required overall height of suction control chamber of the chest drainage device while maintaining same operational range as prior chest drainage devices.

21 Claims, 2 Drawing Sheets

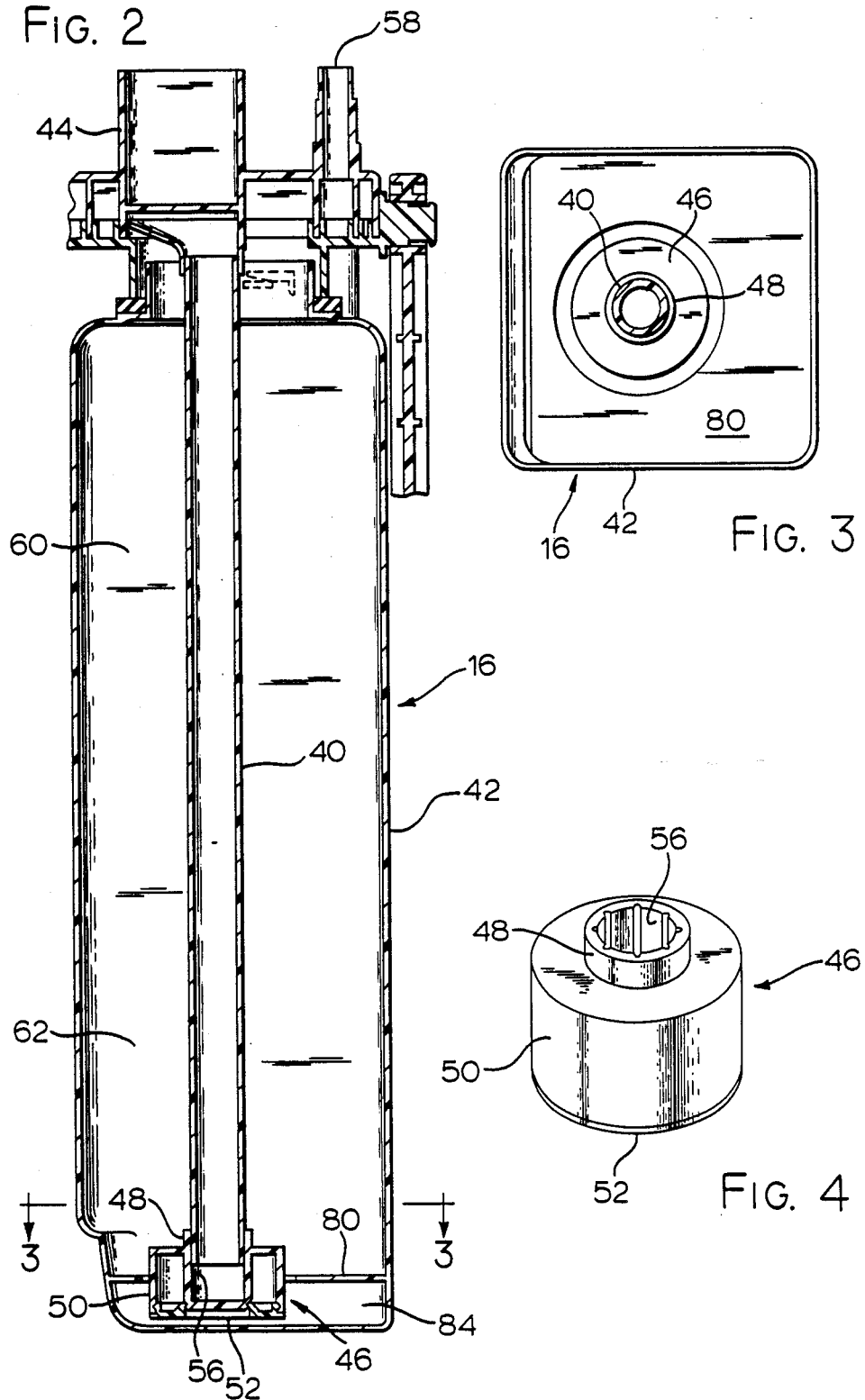

FLOATATION CHAMBER FOR USE IN A CHEST DRAINAGE DEVICE

THE FIELD OF THE INVENTION

This invention relates to chest drainage devices and more particularly to an improved suction control chamber design wherein the overall height of the chest drainage unit may be reduced while allowing the suction control chamber to produce the desired negative pressure in the patient's pleural cavity.

BACKGROUND OF THE INVENTION

Chest drainage devices are used primarily for removing fluids from the pleural cavity of a patient and generally include a collection chamber a water seal chamber and a suction control chamber. The suction control chamber limits the negative pressure applied to the collection chamber and the pleural cavity of the patient. During operation of a chest drainage device, liquid from the patient's pleural cavity is drawn into and accumulated in the collection chamber. The gas is drawn from the pleural cavity of the patient passed through a water seal in the water seal chamber and into the source of suction. The water seal operates as a barrier to prevent the patient's pleural cavity from being exposed to the atmosphere and also prevents the patient's pleural cavity from being in direct flow communication with the source of suction.

U.S. Pat. No. 3,783,780, issued to Schachet on Jan. 8, 1974, and U.S. Pat. No. 4,439,190, issued to Protzmann et al on March 27, 1984 describe the operation of a typical chest drainage device. Both of the above referenced patents are incorporated herein by reference. The present invention is readily adaptable for use in an integral one piece chest drainage device or a multi bottle chest drainage device similar to the chest drainage devices referenced above.

Generally, the suction control chamber allows the user to apply a prescribed pressure to the pleural cavity of a patient by adding a predetermined amount of liquid to the suction control chamber. The commonly used chest drainage device utilizes a suction control chamber which is basically an unequal legged water manometer to regulate the vacuum pressure being applied to the pleural cavity of a patient. This type of suction control chamber generally consists of a pair of legs or columns interconnected at their bottom ends. The top of the generally smaller, first column, is open to the atmosphere. The second column is generally larger than the first column and includes a top end in flow communication with the vacuum source and the pleural cavity of the patient.

The overall height of the suction control chamber typically dictates the minimum height of the chest drainage device. Commonly available chest drainage devices have an overall height of approximately 40 cm. and in the typical suction control chamber, approximately 25 cm. is attributable to the operational range of the chest drainage device described herein as the suction control section. The remaining height of the chest drainage device is attributable to the air/water separation space located above the suction control section and the height of the base or stand of the chest drainage device.

The effectiveness of the air/water separation space at any given air flow rate is determined by the overall suction control chamber geometry and the height of the suction control chamber above the suction control section. If the air flow rate through the suction control chamber is too high, liquid is entrained in the air and will be carried out of the suction control chamber. If this occurs, the suction pressure being applied to the pleural cavity of the patient will gradually decrease as the liquid level in the suction control chamber is depleted. Additionally, the liquid from the suction control chamber will contaminate the vacuum source and/or be deposited within the other chambers of the chest drainage device. Certain chest drainage devices have incorporated baffles in the top of the suction control chamber in an effort to decrease the required height of the air/water separation space and to prevent the loss of water in the suction control chamber.

In a chest drainage device, the vacuum pressure applied to the pleural cavity of a patient is dependent of the dynamic water height of the liquid in the suction control chamber. For example, if the desired patient pressure is 20 cm. $H_2O$ of vacuum pressure, a dynamic water height of at least 20 cm. is required in the suction control chamber. In chest drainage devices which utilize a water seal chamber, the water seal chamber will typically add approximately 2 cm. of resistance so that if the desired patient pressure is 20 cm. $H_2O$, the suction control chamber must provide 22 cm. $H_2O$ of vacuum pressure to overcome the increased resistance created by the water seal chamber. The standard operating ranges for most chest drainage devices is between 5 and 25 cm. $H_2O$ vacuum pressure. Therefore, in order to have the capability of supplying the 25 cm. $H_2O$ of vacuum pressure to the pleural cavity of the patient, this portion of the suction control chamber must be at least 25 cm. high. The baffle systems used in certain chest drainage devices are designed to reduce the height of the air/water separation space and do not materially effect the dynamic water height of the suction control chamber. Therefore, unless valves or other flow restricting devices are used, the height of a chest drainage device must be at least 25 cm. plus the height of the air/water separation space or baffle chamber in the base of the chest drainage device.

SUMMARY OF THE INVENTION

An object of the present invention is to provide an improved suction control chamber wherein the overall height of the chest drainage device may be reduced.

A further object of the present invention is to provide a chest drainage device wherein the actual suction pressure being applied to the patient is readily ascertainable.

Still another object of the present invention is to provide an improved suction control chamber which is readily adaptable for use in nearly any chest drainage device.

Still another object of the present invention is to provide a chest drainage device having a greater operational range than presently available chest drainage devices without increasing the overall height of the chest drainage device.

In accordance with one form of the present invention, the improved chest drainage device is a type of chest drainage device typically known as a three bottle chest drainage device. Thus, the improved chest drainage device of the present invention preferably includes a collection chamber adapted to be in fluid communication with the patient's pleural cavity; a water seal chamber in flow communication with the collection chamber; and an improved suction control chamber. Additionally, the illustrated form of the present invention includes a manifold which maintains flow communication among the various chambers.

The suction control chamber of the present invention is comprised of a pair of generally elongate columns in fluid communication at their bottom ends. The smaller first column extends downwardly into the larger, second column. The top end of the first column is open to the atmosphere while the bottom end of the first column includes a movable float generally connected in flow communication with the bottom opening of the first column.

In the preferred embodiment, the second column is larger than the first column and substantially encloses the first column. The top end of the second column is in flow communication with the vacuum source and the pleural cavity of the patient. The height of the second column is generally divisible into two sections, the first section is the air/water separation space and is located near the top end of the second column. The second section is the suction control section which extends from the bottom end of the suction control chamber upwardly to the air/water separation space. The section is the portion of the suction control chamber which is typically prefilled with liquid to provide the dynamic water height that controls the amount of vacuum pressure that is actually being applied to the pleural cavity of the patient.

In another form of the present invention, a damper chamber is formed in the bottom of the suction control section to stabilize movement of the float chamber during operation of the chest drainage device. In this embodiment, whenever the float chamber moves downwardly away from the bottom of the first column, liquid must be displaced in the bottom of the damper chamber. When the float chamber moves upwardly toward the first column, the space occupied by the float chamber must be replaced by a liquid from the suction control section which flows downwardly into the damper chamber.

An advantage of the present invention is that the improved suction control chamber allows for the construction of a versatile chest drainage device which has either a smaller overall height than the presently available chest drainage devices or has a larger operating capacity than presently available chest drainage devices without increasing the height of the chest drainage device.

Another advantage of the improved suction control chamber is that it is readily adaptable for use on nearly any chest drainage device.

These, as well as other features and advantages of the present invention will become apparent from the following detailed description and accompanying drawings.

BRIEF DESCRIPTION OF THE DRAWINGS

FIG. 2 is an enlarged cross sectional view of an alternate embodiment of the suction control chamber of the present invention;

FIG. 3 is a cross sectional view taken along lines 3—3 of FIG. 2; and

FIG. 4 is a perspective view of the float chamber of the present invention.

DETAILED DESCRIPTION OF THE PREFERRED EMBODIMENT

Figure 1:
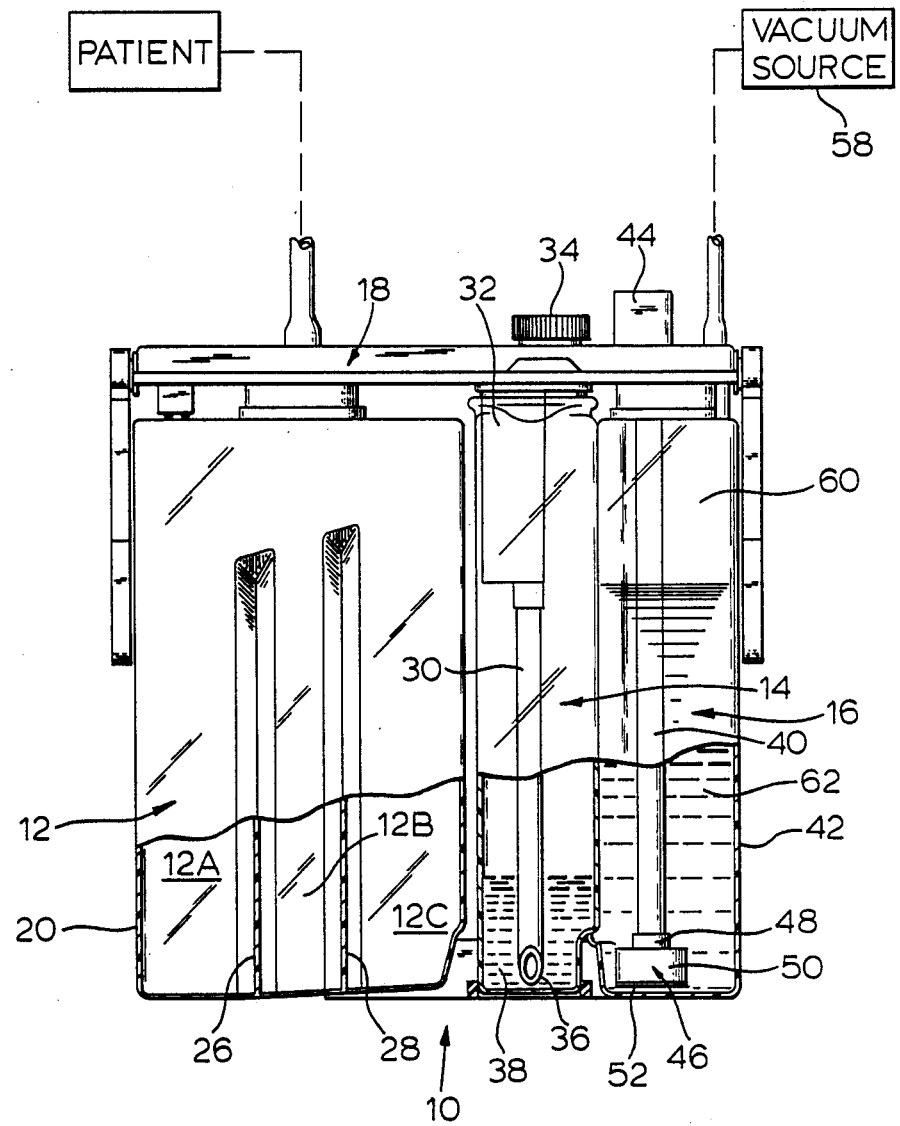
FIG. 1 is a cross-sectional side view of the preferred embodiment of the present invention.

A preferred design of the present invention is illustrated in the attached drawings and is designated herein, generally, as chest drainage device 10. The chest drainage device of the present invention consists primarily of a collection chamber 12, water seal chamber 14, a suction control chamber 16 and a manifold 18. In the preferred embodiment, the manifold 18 is attached to the top of the collection chamber 12 and the suction control chamber 16 is attached to the manifold 18 adjacent to the water seal chamber 14. The manifold 18 provides the desired flow communication between the collection chamber 12, the water seal chamber 14 and the suction control chamber 16, thus, eliminating the need for hoses, conduits and the like frequently used in a variety of other chest drainage devices.

In order to provide for the accurate measurement of the fluid collected from the pleural cavity of the patient, the collection chamber is provided with inner walls 26 and 28, which, in combination with the outer walls 20, divide the collection chamber 12 into three compartments, 12A, 12B, and 12C. The height of wall 26 is less than the wall 28 so that once compartment 12A is filled, fluid will flow into 12B, after compartment 12B is filled, fluid will flow into spill over into compartment 12C. Each compartment has graduations thereon so that the attending physician or nurse can readily determine the amount of drainage collected from the pleural cavity of the patient.

The water seal chamber 14 includes a water seal column 30 and a baffle chamber designated generally as 32. Liquid is poured into the water seal chamber 14 through the fill cap 34 until it reaches the fill line indicated on the side of the water seal chamber 14. The volume of liquid placed in the water seal chamber 14 should be sufficient to continuously cover the bottom opening 36 of the water seal column 30 during the typically operation of the chest drainage device 10. This, volume of liquid is commonly known as a water seal and is referred herein as the water seal 38.

The suction control chamber 16 includes a generally cylindrical first column 40 which is surrounded and substantially enclosed by a larger second column 42. The top end of the first column 40 includes a fill opening 44 which is open to the atmosphere and allows liquid to be poured into the suction control chamber 16. The first column 40 extends downwardly into the suction control chamber 16 from the fill opening 44 to a float chamber 46 which movably contacts the open bottom end of the first column 40. The float chamber 46 consists of a retaining ridge 48 on the top surface thereof; a body section 50 and a lower base section 52. The body section 50 includes a centrally positioned recess 56 which slidably receives the bottom end of the first column 40. The inner diameter of the recess 56 is slightly larger than the outer diameter of the first column to allow air to pass therebetween. The retaining ridge 48 extends upwardly from the body section 50 to further retain the first column 40 therein and to maintain the float chamber 46 in a slidable, generally contacting relation with the bottom end of the first column. The body section 50 and the base section 52 cooperate to create a float chamber 46 having a precisely defined buoyancy.

The second column 42 of this embodiment includes a top end in flow communication with the vacuum source 58 and the pleural cavity of the patient through a variety of passageways in the manifold 18. The bottom end of the second column 42 is in flow communication with the bottom end of the first column 40 and the float chamber 46. The second column 42 is generally divisible into two sections; the top section is the air/water separation space 60 and the lower, second section, is the suction control section 62. The air/water separation space 60 operates to prevent liquid from being drawn into the vacuum source 58 or into the collection chamber 12 of the chest drainage device 10. The height of the air/water space 60 in the preferred embodiment, is typically 10–17 cm. high and may be reduced through the use of a variety of baffles (not shown) or by modifying the overall geometry of the suction control chamber 16.

The lower section of the second column 42 is the suction control section 62. This section of the second column 42 creates the dynamic water height of the liquid in the suction control chamber 16 and determines the amount of vacuum pressure actually applied to the pleural cavity of the patient. The typical chest drainage device applies between 5 and 25 cm. $H_2O$ to the pleural cavity of the patient and therefore the minimum height of the suction control section 62 is typically 25 cm. In the present invention, when liquid is added to the suction control chamber 16, the volume and buoyancy of the float chamber 46 decreases the amount of liquid necessary to create the desired dynamic water height and therefore the overall height of the suction control section may be reduced to produce the desired patient vacuum pressure.

For example, in the typical suction control chamber 16, liquid is added to the bottom of the suction control chamber 16 to a desired level corresponding to the amount of vacuum pressure to be applied to the pleural cavity of the patient. This is commonly known as the dynamic water height of the suction control chamber 16. At this level, the hydrostatic pressures in the second column 42 cause a certain amount of liquid to flow upwardly into the bottom of the first column 40 until the upward pressure is balanced by the downward pressure in the first column 40. This downward pressure is caused by the atmospheric pressure which enters the first column through the top fill opening 44. During operation of the chest drainage device 10, the vacuum source 58 applies a vacuum pressure to the top of the second column 42 and causes the liquid to be drawn from the first column 40 into the bottom section of the second column 42. As this occurs, air is pushed by atmospheric pressure into the suction control chamber 16 through the first column 40 and into the second column 42 to offset the pressure difference between the dynamic water height of the column and the vacuum pressure being applied by the vacuum source 58.

The float chamber 46 of the present invention normally operates to apply a buoyant force to the bottom opening of the first column 40. This buoyant force is directed upwardly against the bottom of the first column 40 and provides an added second force in addition to the dynamic water height of the suction control chamber 16 that must be overcome before air is pushed into the suction control chamber 16. When the vacuum source 58 applies a vacuum pressure in excess of the dynamic water height of the suction control chamber 16 and the buoyant force of the float chamber 46, air is pushed into the suction control chamber 16 through the first column 40 to offset the difference. Therefore, if the liquid in the suction control chamber 16 provides a dynamic water height of approximately 15 cm. $H_2O$ and the float chamber 46 applies a buoyancy force equivalent to 5 cm. a vacuum pressure in excess of 20 cm. $H_2O$ will be required before air is pushed into the suction control chamber 16 through the first column 40 by the atmosphere. Therefore, by decreasing the required dynamic water height of the suction control chamber 16 by 5 cm. the overall height of the suction control chamber 16 and chest drainage device 10 may also be reduced by approximately 5 cm.

This capability is also useful where it is desirable to increase the operating range of the suction control chamber 16 without increasing the overall height of the suction control chamber 16. In the past, it was necessary to add a separate vacuum regulator and bypass the suction control chamber 16 to obtain higher vacuum pressures. With the present invention, it is possible to design a suction control chamber 16 capable of applying higher vacuum pressures to the pleural cavity of the patient without significantly increasing the overall height of the suction control chamber 16 by using a float chamber of the type described herein.

In the second embodiment illustrated in FIG. 2, a damper 80 is used to create a substantially closed damper chamber 84 adjacent to the body section 50 of the float chamber 46. The damper 80 of this embodiment consists of an inwardly directed ridge in the bottom of the suction control chamber 16 which extends inwardly from the side of the suction control chamber to a location adjacent in the float chamber 46. The use of the damper 80 will decrease pressure fluctuations caused by erratic movement between the float chamber 46 and the bottom of the first column 40. When the float chamber 46 moves downwardly from the bottom of the first column 40, liquid in the damper chamber 84 must be displaced to allow for the downward movement of the float chamber 48. In order for this to occur, liquid in the damper chamber 84 must flow around the sides of the float chamber 46 and past the damper 80. Likewise, when the float chamber 46 moves upwardly, liquid must flow downwardly into the area of the damper chamber 84 vacated by the float chamber 46.

The chest drainage device 10 of the present invention functions similar to other chest drainage devices and is briefly discussed herein to assist in describing the overall operation of the present chest drainage device 10. Operation of the chest drainage device 10 of the present invention includes the preliminary steps of adding a predetermined amount of liquid to the water seal chamber 14 to create the water seal 38 and adding a predetermined amount of liquid to the suction control section 62 of the suction control chamber 16 to a level sufficient to provide the desired patient vacuum pressure. Once the vacuum hose 70 is attached to the vacuum source 56 and the drainage tube 24 is attached to the patient's pleural cavity, the process of suctioning fluid from the patient's pleural cavity is begun. If the vacuum pressure from the vacuum source 56 exceeds the prescribed patient vacuum level, atmospheric air is pushed into the suction control chamber 16 through the fill opening 44; into the first column 40 and past the float chamber 46 into the second column 42 to decrease the vacuum pressure actually applied to the pleural cavity of the patient.

During normal operation of the chest drainage device 10, the water seal 38 in the water seal chamber 14 may be drawn upwardly in the water seal column whenever the patient inspires (negative pressure). The liquid will flow downwardly in the water seal column 30 and into the reservoir area 33 of the water seal chamber 14 whenever the patient breathes out (positive pressure). As the fluid is drawn from the patient's pleural cavity, the liquid is collected in the collection chamber 12 and any gases drawn from the pleural cavity of the patient will flow through the water seal chamber 14 and into the vacuum source 56. As described previously, the operation of the water seal chamber adds approximately 2 cm. $H_2O$ of resistance so that the typical suction control chamber 16 must provide approximately 22 cm. $H_2O$ of vacuum pressure to overcome the additional resistance created by the operation of the water seal chamber 14.

While the preferred form of the invention has been described with reference to one specific type of drainage device, it will be apparent that various changes and modifications thereto may be made without departing from the true scope of the invention as defined by the following claims. For example, the general shape or design of float chamber 46 may be readily modified to be adaptable for use with nearly any suction control chamber design as long as the float chamber is able to apply a buoyant force to the equivalent of a first column and is movable to allow air or liquid to flow between the respective columns. Additionally, it is readily anticipated that the suction control chamber of the present invention may be an integral part of a chest drainage device or a separate suction control chamber which may be connected to nearly any chest drainage device without substantial modification or alteration of the present invention.

What is claimed is:

1. A chest drainage device for removing fluids and gases from the body of a patient comprising,
   a collection chamber in flow communication with the body of a patient wherein fluids from the body of a patient will be collected therein,
   a source of vacuum pressure in flow communication with said collection chamber to apply a desired vacuum pressure to the body of a patient to draw fluids into said collection chamber,
   a liquid containing suction control chamber in flow communication with the atmosphere and said source of vacuum pressure,
   said suction control chamber having first and second columns formed therein and said first and second columns having top ends and bottom ends and wherein said bottom ends are in flow communication with each other and said top end of said first column is in flow communication with the atmosphere and said top end of said second column is in flow communication with said source of vacuum pressure, and
   a float means in flow communication with said first column wherein said float means selectively restricts the flow of fluid in said suction control chamber to regulate the amount of vacuum pressure applied to the body of a patient by said source of vacuum pressure.

2. The device of claim 1, wherein said float means comprises a buoyant float member operationally positioned in the liquid contained in said suction control chamber and in flow communication with said bottom end of the said first column.

3. The device of claim 2, wherein said suction control chamber further includes a damper member extending inwardly into said suction control chamber to a position adjacent to said float member to form a lower chamber section to inhibit the flow of liquid in said suction control chamber adjacent said first column.

4. The device of claim 1, wherein said float means comprises a float member which selectively blocks the flow of air through said bottom end of said first column in response to the difference between the desired vacuum pressure applied to the body of a patient and the vacuum pressure applied to said suction control chamber by said source of vacuum pressure.

5. The device of claim 4, wherein said float member allows atmospheric air to be pushed into said suction control chamber through said first column when the vacuum pressure applied by said source of vacuum pressure is greater than the desired patient vacuum pressure.

6. A chest drainage device for removing fluids and gases from the body of a patient comprising,
   a collection chamber in flow communication with the body of a patient wherein fluids from the body of a patient will be collected therein,
   a source of vacuum pressure in flow communication with said collection chamber to apply a desired vacuum pressure to the body of a patient to draw fluids into said collection chamber,
   a liquid containing suction control chamber in flow communication with the atmosphere and said source of vacuum pressure,
   said suction control chamber having first and second columns formed therein and said first and second columns having top ends and bottom ends and wherein said bottom ends are in flow communication with each other and said top end of said first column is in flow communication with the atmosphere and said top end of said second column is in flow communication with said source of vacuum pressure, and
   a float means in flow communication with said first column wherein said float means restricts the flow of fluid in said suction control chamber between the first and second columns, and
   wherein the liquid in said suction control chamber forms a dynamic water height between said first and second columns to resist the flow of air from the atmosphere into said suction control chamber and said float means provides an additive buoyant force to resist the flow of air from the atmosphere into said suction control chamber.

7. The device of claim 1, wherein liquid containing water seal chamber is positioned in flow communication with said collection chamber and said source of vacuum pressure and said second column is formed by the interior surface of said suction control chamber such that said second column substantially encloses said first column.

8. A suction control chamber assembly in flow communication with a collection chamber of a drainage device for removing fluids from the body of a patient, wherein the suction control chamber assembly comprises,
   a first column having top and bottom ends wherein said top end is in flow communication with the atmosphere,
   a second column having top and bottom ends wherein said bottom end is flow communication with said first column and said top end is in flow communication with a source of vacuum pressure, and a float means buoyantly in flow communication with said first column to selectively restrict flow communication between the source of vacuum pressure and the atmosphere to regulate the amount of vacuum pressure applied to the body of a patient.

9. The suction control chamber assembly of claim 8, wherein said suction control chamber assembly has top and bottom ends and wherein a liquid is placed in said suction control chamber assembly to selectively submerge said float means in the liquid in response to the difference between desired vacuum pressure to be applied to the body of a patient and the vacuum pressure applied by said source of vacuum pressure to said suction control chamber assembly.

10. A suction control chamber in flow communication with a collection chamber of a drainage device for removing fluids from the body of a patient, wherein said suction control chamber comprises,
    a first column having top and bottom ends wherein said top end is in flow communication with the atmosphere,
    a second column having top and bottom ends wherein said bottom end is in flow communication with said first column and said top end is in flow communication with a source of vacuum pressure,
    a float chamber in flow communication with said first column to selectively restrict flow communication between the source of vacuum pressure and the atmosphere, and
    wherein said float chamber selectively restricts flow communication between the bottom end of said first column and the second column when said float chamber is at least partially submerged in a liquid contained in said suction control chamber.

11. The suction control chamber assembly of claim 8, wherein said suction control chamber assembly further includes sidewalls and a damper member extending inwardly therefrom near the bottom end of said suction control chamber assembly to form a liquid flow restricting chamber therein to inhibit the flow of a liquid contained in the bottom end of said suction control chamber.

12. The suction control chamber assembly of claim 11, wherein said damper member extends inwardly from sidewalls of said suction control chamber assembly to a location adjacent to said float means.

13. A suction control chamber in flow communication with a collection chamber of a drainage device for removing fluids from the body of a patient, wherein the suction control chamber comprises,
    a first column having top and bottom ends wherein said top end is in flow communication with the atmosphere;
    a second column substantially enclosing said first column and having top and bottom ends wherein said top end is in flow communication with a source of suction and said bottom end is in flow communication with said first column, and
    a float means in said second column buoyantly in flow communication with said first column to selectively regulate the flow communication between said source of suction and the atmosphere by selectively allowing the flow of atmosphere into said second column.

14. The suction control chamber of claim 13, wherein a liquid is placed in the bottom of said second column to at least partially submerge said float means and wherein said float means is buoyant in said liquid to selectively restrict the flow of atmosphere through said first column.

15. A suction control chamber in flow communication with a collection chamber of a drainage device for removing fluids from the body of a patient, wherein the suction control chamber comprises,
    a first column having top and bottom ends wherein said top end is in flow communication with the atmosphere.
    a second column substantially enclosing said first column and having top and bottom ends wherein said top end is in flow communication with a source of suction and said bottom end is in flow communication with said first column,
    a float chamber in said second column and in flow communication with said first column to selectively restrict flow communication between the source of suction and the atmosphere, and
    wherein said float chamber selectively restricts flow communication between said bottom end of said second column and the atmosphere.

16. The suction control chamber of claim 13, wherein said second column includes a damper means in the bottom end thereof adjacent to said float means to inhibit the flow of a liquid contained in said second column.

17. A suction control chamber in flow communication with a collection chamber of a drainage device for removing fluids from the body of a patient, wherein said suction control chamber comprises,
    a first column having top and bottom ends wherein said top end is in flow communication with the atmosphere;
    a second column substantially enclosing said first column and having top and bottom ends wherein said top end is in flow communication with a source of suction and said bottom end is in flow communication with said first column,
    a float chamber in said second column and in flow communication with said first column to selectively restrict the flow communication between said source of suction and the atmosphere, and
    wherein said float chamber selectively restricts said bottom end of said first column in response to the pressure difference between the suction pressure applied by the source of suction and the atmospheric pressure applied through said first column.

18. A suction control chamber in flow communication with a collection chamber of a drainage device for removing fluids from the body of a patient, wherein the suction control chamber comprises,
    a first column having top and bottom ends wherein said top end is in flow communication with the atmosphere,
    a second column substantially enclosing said first column and having top and bottom ends wherein said to end is in flow communication with a source of suction and said bottom end is in flow communication with said first column,
    a float chamber in said second column and in flow communication with said first column to selectively restrict flow communication between the source of suction and the atmosphere, and
    wherein said float chamber selectively obstructs said bottom end of said first column when the atmospheric pressure is less than the pressure in said second column.

19. A drainage device for removing fluids and gases from the body of the patient comprising:
- a collection chamber in flow communication with the body of a patient wherein fluids from the body of a patient will be collected therein,
- a source of vacuum pressure in flow communication with said collection chamber to apply a desired vacuum pressure to the body of a patient to draw fluids into said collection chamber,
- a suction control chamber in flow communication with the atmosphere and said source of vacuum pressure to regulate the amount of vacuum pressure to the body of a patient,
- said suction control chamber including a first column having top and bottom ends wherein said top end is in flow communication with the atmosphere, and
- a float means operationally positioned in said suction control chamber to selectively restrict flow of the atmosphere through said first column in response to the difference between the desired vacuum pressure and the vacuum pressure applied by said source of vacuum pressure to regulate the amount of vacuum pressure applied to the body of a patient by said source of vacuum pressure.

20. A drainage device for removing fluids and gases from the body of a patient comprising;
- a collection chamber in flow communication with the body of a patient wherein fluids form the body of a patient will be collected therein,
- a source of vacuum pressure in flow communication with said collection chamber to apply a desired vacuum pressure to the body of a patient to draw fluids into said collection chamber,
- a liquid containing suction control chamber in flow communication with the atmosphere and said source of vacuum pressure to regulate the amount of vacuum pressure applied by said source of vacuum pressure to the body of a patient,
- said suction control chamber including a first member having top and bottom ends wherein said top end is in flow communication with the atmosphere and wherein the liquid in said suction control chamber forms a dynamic water height in said suction control chamber to resist the flow of atmosphere through said first member, and
- a float means operationally positioned in said suction control chamber to provide an additive buoyant force to resist the flow of atmosphere through said first member.

21. The drainage device of claim 20, wherein said float means is adjacent said bottom end of said first member and the buoyant force of said float means selectively restricts the flow of liquid from said suction control chamber into said first member.

* * * * *